(12) United States Patent
Haji

(10) Patent No.: US 12,285,709 B2
(45) Date of Patent: *Apr. 29, 2025

(54) APPARATUS FOR AIR PURIFICATION AND SANITIZATION

(71) Applicant: Next Gen Design and Development LLC, Ferndale, MI (US)

(72) Inventor: Hadir Haji, Bloomfield Township, MI (US)

(73) Assignee: Next Gen Design and Development LLC, Bloomfield Township, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/583,106

(22) Filed: Feb. 21, 2024

(65) Prior Publication Data

US 2024/0226789 A1 Jul. 11, 2024

Related U.S. Application Data

(63) Continuation of application No. 17/121,822, filed on Dec. 15, 2020, now Pat. No. 11,911,722.

(51) Int. Cl.
*B01D 46/00* (2022.01)
*A61L 2/00* (2006.01)
(Continued)

(52) U.S. Cl.
CPC ........ *B01D 46/0028* (2013.01); *A61L 2/0088* (2013.01); *A61L 2/24* (2013.01); *A61L 9/014* (2013.01); *B01D 46/0004* (2013.01); *B01D 46/0043* (2013.01); *B01D 46/0049* (2013.01); *B01D 46/4245* (2013.01);
(Continued)

(58) Field of Classification Search
CPC .......... A61L 2/0088; A61L 2/24; A61L 9/014; A61L 2202/14; A61L 2202/15; A61L 2209/111; A61L 2209/14; A61L 2209/22; B01D 46/0028; B01D 46/0043;
(Continued)

(56) References Cited

U.S. PATENT DOCUMENTS 6,189,740 B1 2/2001 Wade et al.
6,354,469 B1 3/2002 Pozzi
(Continued)

FOREIGN PATENT DOCUMENTS

WO 2018019592 A1 2/2018
WO 2022003724 A1 1/2022

*Primary Examiner* — Robert Clemente
(74) *Attorney, Agent, or Firm* — Dickinson Wright PLLC

(57) ABSTRACT

An apparatus configured to purify air and sanitizing including a main base including one or more buttons configured to operate the apparatus, a lid attachable to the main base and that includes one or more ventilation perforations to intake air and an orifice to output purified air, a filter adjacent to the one or more ventilation perforations and enclosed in the lid, wherein the filter is configured to remove at least bacteria from atmospheric air and extract purified air, a fan configured to intake atmospheric air into the filter and blow purified air extracted from the filter outside of an orifice of the lid, a tank configured to store liquid, wherein the liquid includes at least liquid sanitizer, a pump configured to output liquid stored in a tank, and a cavity section that includes an outlet configured to output the liquid sanitizer in response to actuation of the pump.

20 Claims, 5 Drawing Sheets

(51) Int. Cl.
　　　*A61L 2/24*　　　(2006.01)
　　　*A61L 9/014*　　　(2006.01)
　　　*B01D 46/42*　　　(2006.01)

(52) U.S. Cl.
　　　CPC ....... *A61L 2202/14* (2013.01); *A61L 2202/15* (2013.01); *A61L 2209/111* (2013.01); *A61L 2209/14* (2013.01); *A61L 2209/22* (2013.01); *B01D 2273/30* (2013.01); *B01D 2279/65* (2013.01)

(58) Field of Classification Search
　　　CPC ............ B01D 46/0049; B01D 46/0004; B01D 46/4245; B01D 2273/30; B01D 2279/65
　　　See application file for complete search history.

(56) References Cited

U.S. PATENT DOCUMENTS 11,911,722 B2 * 2/2024 Haji .................. B01D 46/4245
2021/0346532 A1 11/2021 Wilson

* cited by examiner

APPARATUS FOR AIR PURIFICATION AND SANITIZATION

CROSS-REFERENCE TO RELATED APPLICATIONS

This application is a continuation of U.S. application Ser. No. 17/121,822 filed Dec. 15, 2020, the disclosure of which is hereby incorporated in its entirety by reference herein.

TECHNICAL FIELD

The following disclosure relates to an air purification and sanitization, such as sanitization of a hand.

BACKGROUND

Studies have shown that many viruses may be transmitted through the air and are thus air borne. Air purifiers may be utilized in order to trap viruses within a filter or other mechanism and delay the transmission of disease. Furthermore, many viruses may be transmitted by contact of various surfaces, including body parts like the human hand and fingers. It has long been known that soap and other sanitizers may aid in destroying the viruses on surfaces (e.g., hard surfaces, human surfaces like the hand, etc.).

SUMMARY

In a first embodiment, an apparatus is configured to purify air and sanitizing including a main base including one or more buttons configured to operate the apparatus, a lid, wherein the lid is attachable to the main base, wherein the lid includes one or more ventilation perforations and an orifice, a filter adjacent to the one or more ventilation perforations and enclosed in the lid, wherein the filter is configured to remove at least bacteria from atmospheric air and extract purified air, a fan configured to intake atmospheric air into the filter and blow purified air extracted from the filter outside of an orifice of the lid, a tank configured to store liquid, wherein the liquid includes at least liquid sanitizer, a pump, wherein the pump is configured to output liquid stored in a tank located in the main base, and a cavity section, wherein the cavity section includes an outlet configured to output the liquid sanitizer in response to actuation of the pump.

In a second embodiment, an apparatus is configured to purify air and sanitize, comprising a lid, wherein the lid is attachable to the main base, wherein the lid includes one or more ventilation perforations to intake air and an orifice to output purified air, a filter adjacent to the one or more ventilation perforations and enclosed in the lid, wherein the filter is configured to remove at least bacteria from atmospheric air and extract purified air, a fan configured to intake atmospheric air into the filter and blow purified air extracted from the filter outside of an orifice of the lid, a tank configured to store liquid, wherein the liquid includes at least liquid sanitizer, a pump, wherein the pump is configured to output liquid stored in a tank located in the main base, and an outlet configured to output the liquid sanitizer in response to actuation of the pump.

In a third embodiment, an apparatus is configured to purify air and sanitize, which includes a main base including one or more buttons configured to operate the apparatus, a lid, wherein the lid includes a bottom that is attachable to a top section of the main base, wherein the lid includes one or more ventilation perforations to intake air and an orifice to output purified air, a filter adjacent to the one or more ventilation perforations and enclosed in the lid, wherein the filter is configured take atmospheric air and extract purified air, a fan configured to intake atmospheric air into the filter and blow purified air extracted from the filter outside of an orifice of the lid, a tank configured to store liquid, wherein the liquid includes at least liquid sanitizer, wherein the tank is attachable to the main base, a pump, wherein the pump is configured to output liquid stored in the tank, and a cavity section, wherein the cavity section includes an outlet configured to output the liquid sanitizer in response to actuation of the pump.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
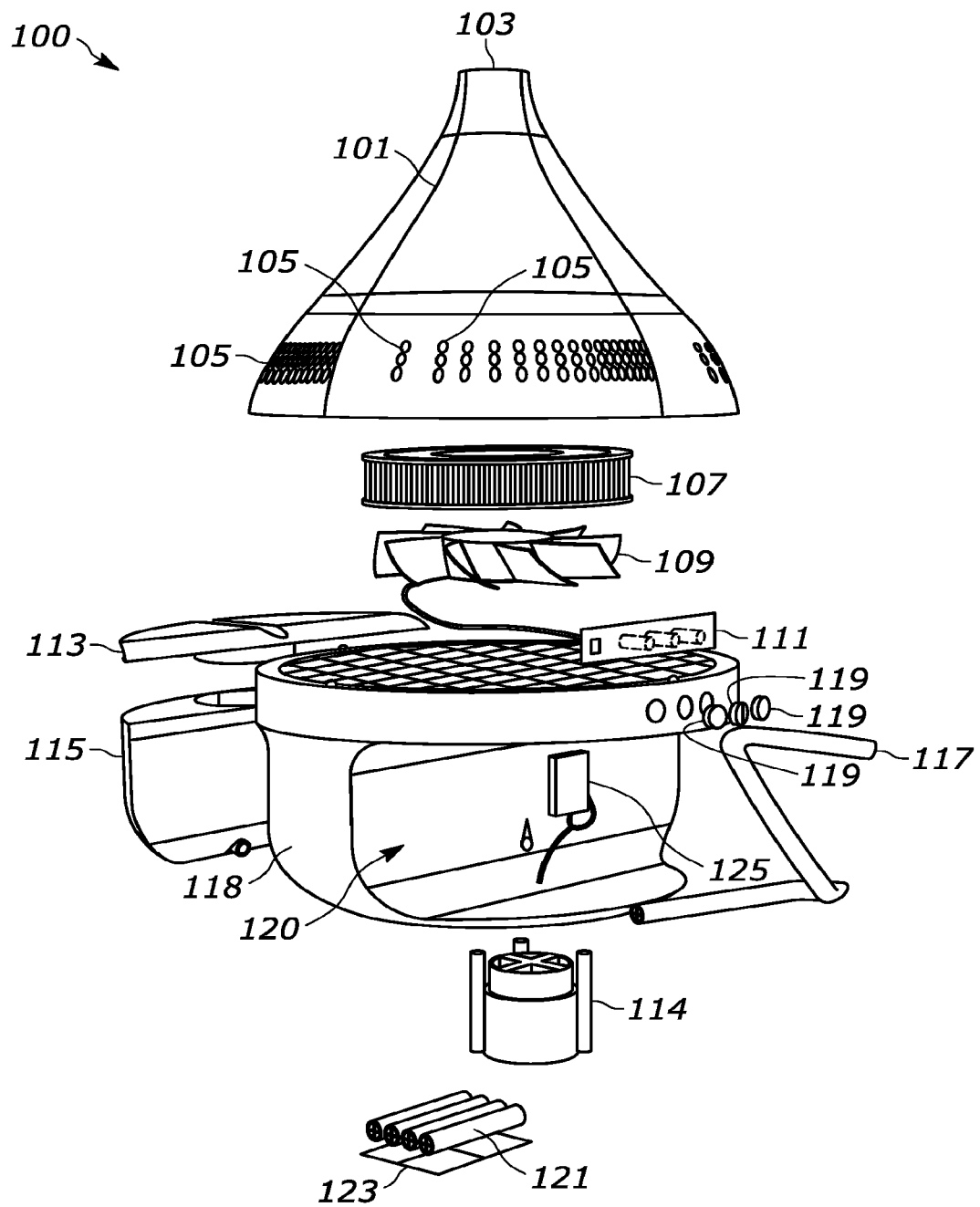
FIG. 1 is an exploded view of an apparatus for sanitization and air purification, including internal components.
Figure 2:
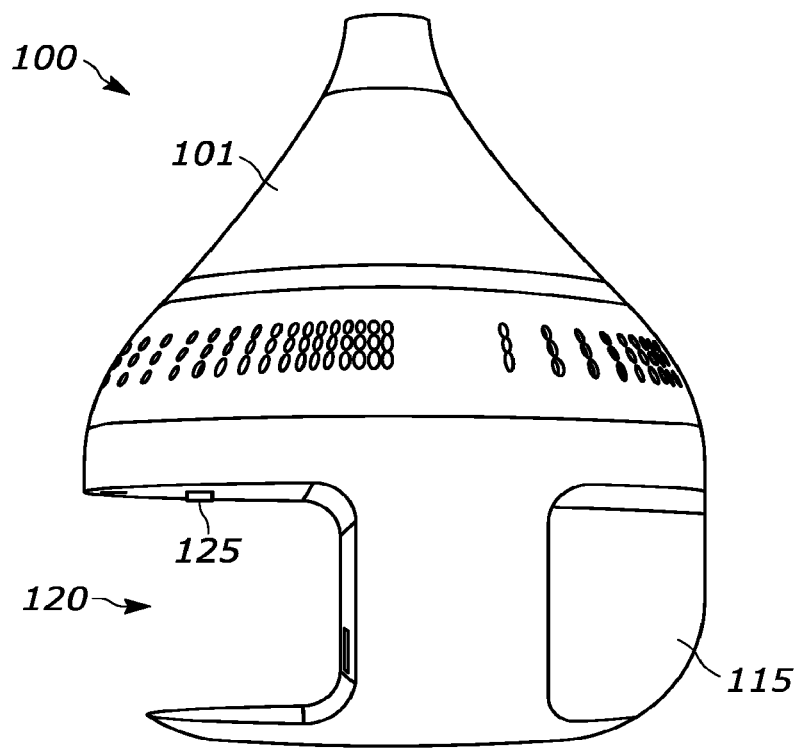
FIG. 2 is a side view of the apparatus.
Figure 3:
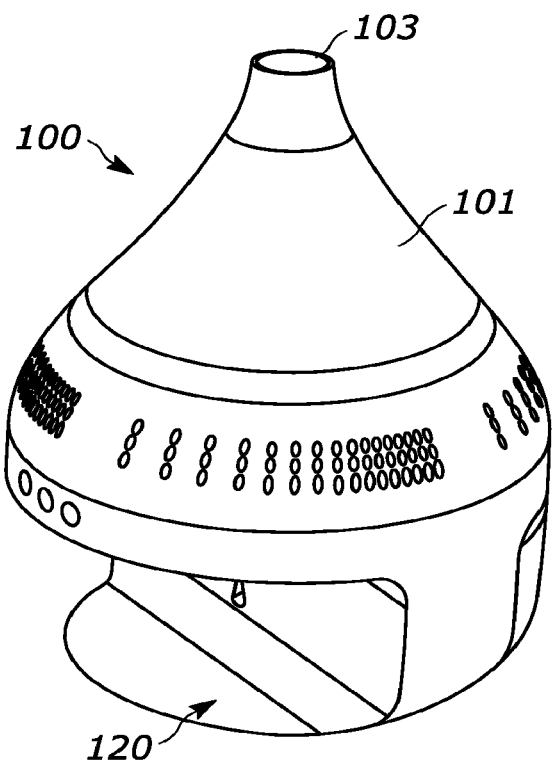
FIG. 3 is a ¾ top view of the apparatus.
Figure 4:
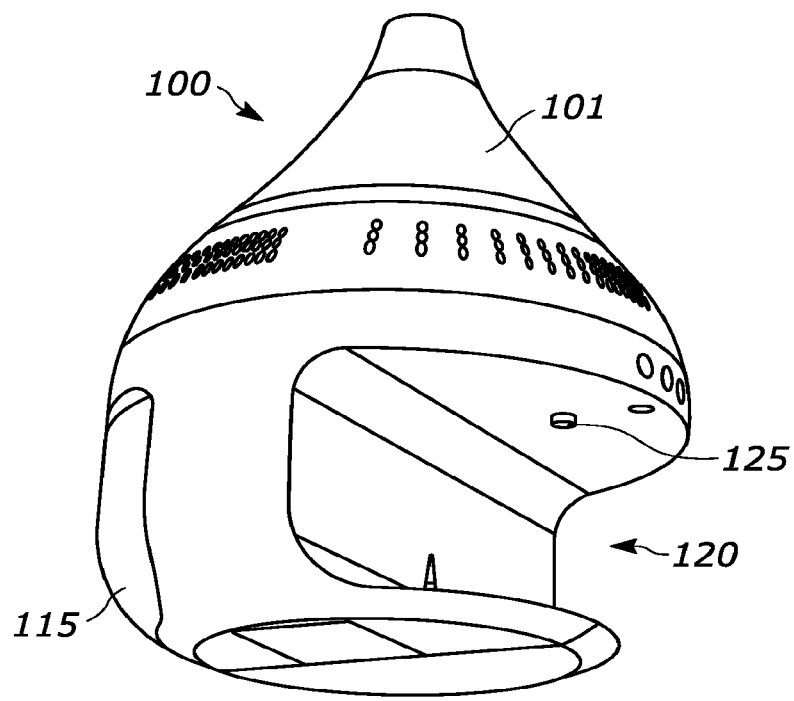
FIG. 4 is a ¾ bottom view of the apparatus.
Figure 5:
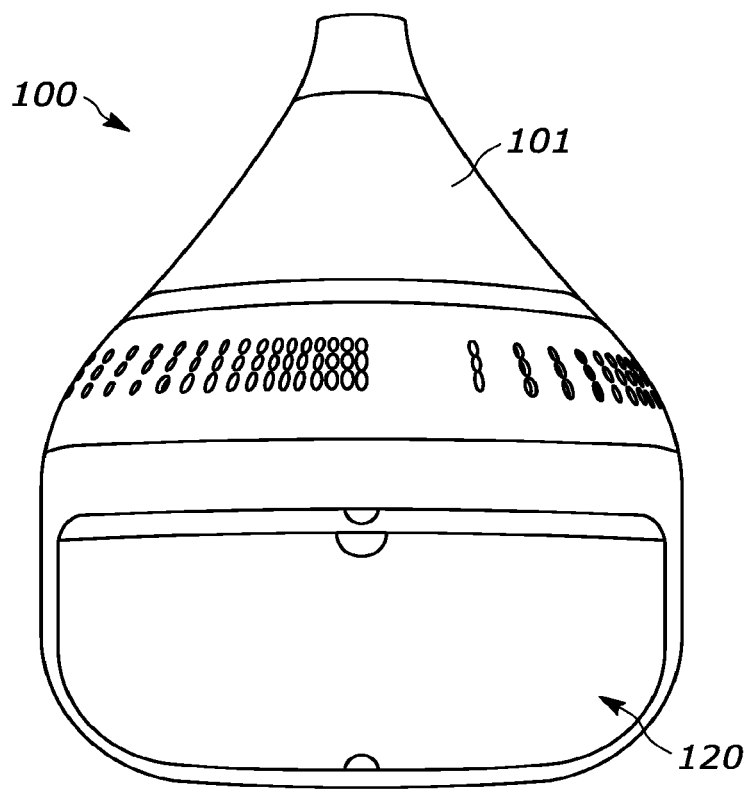
FIG. 5 is a front view of the apparatus.
Figure 6:
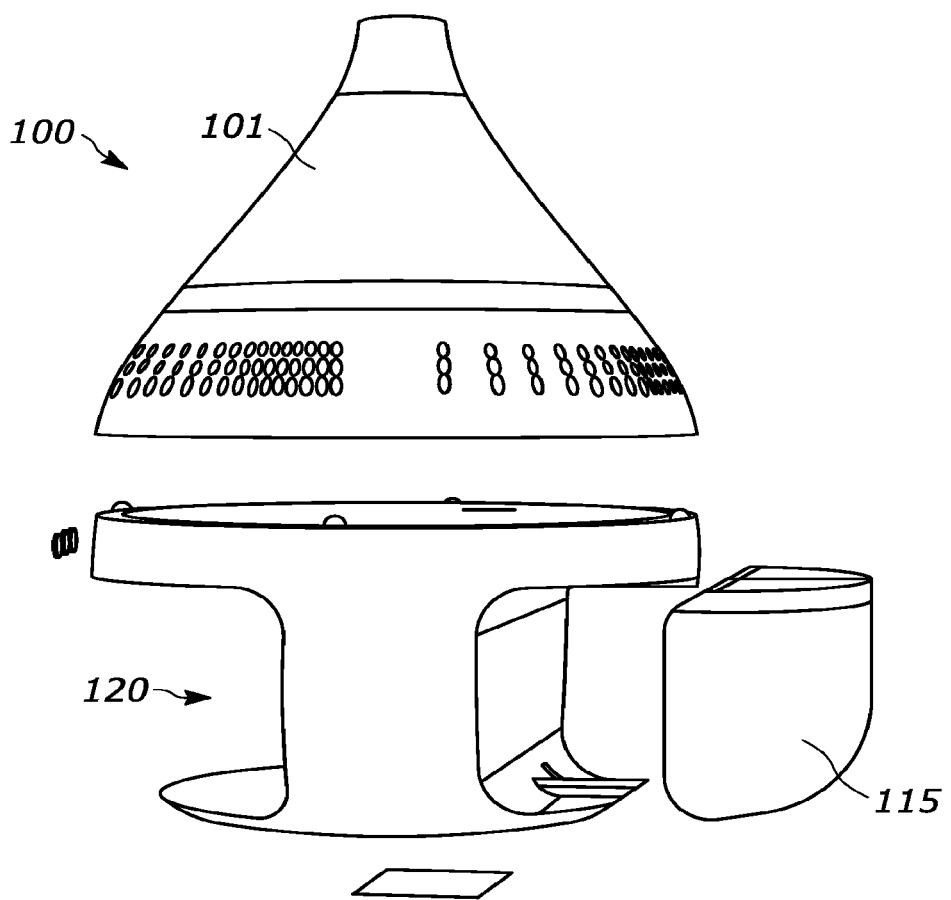
FIG. 6 is an exploded view of external components of the apparatus.

FIG. 1 is an exploded view of an apparatus for sanitization and air purification. The disclosure below may be related to FIGS. 1-7. The air purification and sanitization apparatus 100 may include a removable lid 101. The removable lid 101 may be removed to allow access to the internal components of the apparatus 100. The removable lid 101 may be any shape or size. The lid 101 may also be non-removable in another embodiment. The lid 101 may include an orifice/opening 103 to allow purified air to be pushed out after being purified by the apparatus 100. The orifice 103 may include a netting or trap to prevent larger objects from falling into the apparatus by the removable lid 101. The lid 101 may be conical shape with a smaller diameter at the top orifice 103 but a larger diameter at the bottom of the lid 101.

The removable lid 101 may also include a plurality of vents 105 or perforations 105. The vents 105 may be utilized to suck in the atmospheric/environmental air. The environmental air may include various bacteria, viruses, pollutes, that may be able to be purified via a filter 107 located in the apparatus 100. The filter 107 may be any type of air filter, such as a HEPA (high efficiency particulate filter) filter that allows for 360 degrees of purification. Thus, any air that is entered into the apparatus 100 may be filtered via the filter. The filter 107 may have a hollow center or may include a solid center. The filter 107 is arranged through which filtering of the ambient air takes place, so that a sterile, filtered and germ-free air, ie a highly fine filtered air without bioreactive substances such as fungi, microorganisms or other contaminating particles is introduced into the product container. The filter unit, which is defined in the feed channel of the second filter group, is a sterile air filter with a filter class Hl3, preferably HI 4 or Class I 00 or higher. The sterile air filter is preferably designed as a HEPA filter (high-efficiency particulate air filter) or ULPA filter (ultra-low-penetration air filter), and furthermore preferably the filter unit has a labyrinthine filter channel. Advantageously, the filter unit comprises a sterile air filter, such as an EPA/HEPA or an UPA filter unit with a filter class Hl3, preferably Hl4 or Class 100 or higher. HEPA filters which are particularly suitable for carrying out the invention are so-called HEP A filters (high-efficiency particulate arrestance filters) or so-called ULPA filters (ultra low-penetration air filters). Filters of these classes are used to filter out viruses, respirable dusts, mite eggs or excretions, pollen, smoke particles, asbestos, bacteria, various toxic dusts or aerosols from the air. These filters are commonly used in medical technology, and can be used according to the invention suitable for the production of sterile air, wherein ambient air is forced by fans or compressors through the filter, and the suspended matter and impurities contained therein can be filtered out. Filters of a filter class HI 3 or higher achieve a separation efficiency of 99.95% for the entire air flow, whereby locally at least 99.75% deposition rate of particles of 0.1 µm to 0.3 µrl1 can be achieved. According to the VDMA standard sheet "compressed air quality" (list of recommended unit classes in accordance with ISO 8573-1) VDMA 15390, filters are used for the production of sterile air for a sterile air overlay completely filter out solid impurities in the range of 1 µrl1 to 5 µrl1 and impurities <1 µrl1 can only pass in the range of 1-100 ppm.

The fan 109 may sit on top of the filter 107. The fan 109 may be located closer to the orifice 103 to allow the fan to blow purified air (assuming the filter is installed) out of the orifice 103. The fan 109 may be directly stacked on top of the filter 107. Thus, such a configuration causes a funnel and directs the air upwards at the orifice I 03 due to the fan's I 09 ability to create a suction. In such an embodiment, the fan I 09 and filter I 07 may be similarly shaped and have a substantially similar size or dimensions (e.g., diameter, radius, perimeter, or circumference within +/−5 millimeters). The fan 109, may be disposed within the filter in one embodiment. Thus, turning of the fan 109 or activation of the fan 109 may cause atmospheric air to be sucked into the filter 107. The unpurified air may be sucked into the filter 107 through the lids orifice 103, then through the filter 107, and push the purified air out the perforations 105. In another alternative embodiment, the fan 109 may suck the air through the vents 105/perforations 105. Thus, larger particles may be filtered via the vents 105, while the microparticles may be filtered via filter 107. The vents 105 on the side of the device may be encircled. The vents I 05 may be any size or shape, but may be surrounding the entire diameter of the lid. The vents may align with the location of the filter 107 in one embodiment, or may be offset with the filter 107 in another embodiment. Thus, the filter 107 may be adjacent the vents 105 in one embodiment. In another embodiment, the filter 107 may be attached to the top most portion of the lid. Thus, the filter 107 may be forced to fit on the top portion of the lid via an interference fit, resting on a lip that aligns with the filter 107, or other embodiments to securely attach the filter to the lid.

Figure 7:
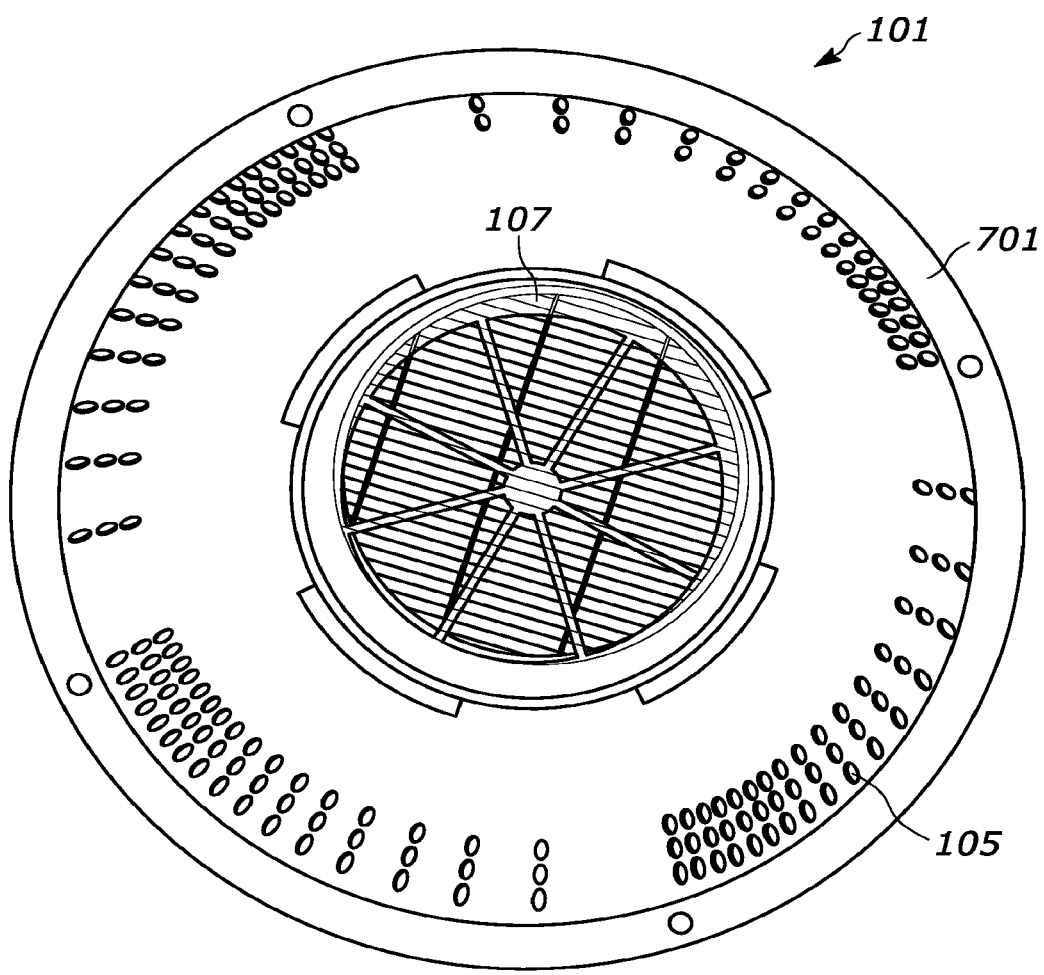
FIG. 7 is an inner view of the lid portion of the apparatus.

As shown in FIG. 7, which discloses an internal view of the lid portion of the apparatus. The lid 101 may include a lip 701 that allows for the resting of the lid 101 on the main base 118. Thus, the lip 701 provides stability and support for the lid 101 to the main base 118. The lip 701 may have holes or fasteners that allow securing of the lid 101 to the main base. In alternative embodiments, other fastening capabilities may be utilized, such as locking mechanisms that require alignment between protrusions and other parts of the lid 101 to the main base 118. As show, the vents 107 may protrude through the inner portion of the lid 101. The filter 107 may be secured to an upper portion of the lid 101 and securely form an interference fit with an upper portion of the lid 101 and the filter 107. Thus, the filter 107 may cover the orifice 103 to only allow air to flow through the filter 107, and not through the sides.

A circuit board 111 or printed circuit board (PCB) 111 may be utilized to control the various electrical and mechanical components of the apparatus 100. The PCB 111 may include a controller or processor. In this disclosure, the terms "controller" and "system" may refer to, be part of, or include processor hardware (shared, dedicated, or group) that executes code and memory hardware (shared, dedicated, or group) that stores code executed by the processor hardware. The "controller" may also be included PCB 111, or may be on another module such as a PCB board that is outside of the apparatus 100 but nonetheless communicates with the apparatus 100. The code is configured to provide the features of the controller and systems described herein. In one example, the PCB and controller may include a processor, memory, and non-volatile storage. The processor may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory. The memory may include a single memory device or a plurality of memory devices including, but not limited to, random access memory ("RAM"), volatile memory, non-volatile memory, static random-access memory ("SRAM"), dynamic random-access memory ("DRAM"), flash memory, cache memory, or any other device capable of storing information. The non-volatile storage may include one or more persistent data storage devices such as a hard drive, optical drive, tape drive, non-volatile solid-state device, or any other device capable of persistently storing information. The processor may be configured to read into memory and execute computer-executable instructions embodying one or more software programs residing in the non-volatile storage. Programs residing in the non-volatile storage may include or be part of an operating system or an application, and may be compiled or interpreted from computer programs created using a variety of programming languages and/or technologies, including, without limitation, and either alone or in combination, Java, C, C++, C#, Objective C, Fortran, Pascal, Java Script, Python, Perl, and PL/SQL. The PCB may be in communication with both the fan 109, buttons 119, and motor 114, as well as a power supply, such as batteries 121. The computer-executable instructions of the programs may be configured, upon execution by the processor, to cause the PCB 111 to command movement of the fan 109 or motor 114 to perform a one of a certain number of available movements.

Buttons 119 may be in communication with or situated on the PCB 111. The buttons 119 may have various options. The buttons 119 may be utilized to power on/off the apparatus, adjust fan speed (e.g., the fan may have three different speeds), adjust dispensing amount of sanitizer, or other options. In one embodiment, the apparatus 100 may allow for turning on the air filtration aspect of the device, but not the sanitizing aspect of the device, or vice versa. In another embodiment, the buttons 119 may be replaced with a touch screen interface. The interface buttons 119 may show activation by emitted lights via an LED or other lighting. Furthermore, the interface buttons 119 may be plastic or mechanical buttons, touch buttons, capacitive touch buttons, haptic feed-back buttons, or any type of button or interface. The buttons 119 may also be associated with or contain lights, such as light emitting diodes, that act to provide information to the user, such as for changing a filter component of the purifier, activation of the fan, low battery power, activation of the sanitizer, etc.

In an alternative embodiment, a Bluetooth module may be implemented on the apparatus 100 to allow remote control of the apparatus 100 utilizing a mobile device such as a cellular phone, tablet, smart watch, etc. In yet another embodiment, the apparatus 100 may include a voice recognition engine situated on the PCB 111 to allow voice commands to control the apparatus 100.

The apparatus 100 may include a main base 118. The main base 118 may include a top surface that is capable of storing the lid 101, as well as the components within the lid 101, such as the filter 107 and fan 109. The main base 118 may also house the buttons 119. In one embodiment, the main base 118 may house the motor, energy storage device, dispenser, circuit board, sensor, and tube. The main base 118 may include a cavity section 120 that may allow for body parts or other items to be placed in to allow sanitizing. An area of the cavity section 120 may host another PCB 111. The PCB in the cavity section 120 may include a motion sensor that allows for recognition of movement or motion. In one example, the motion sensor may have a 0-6 centimeter range to activate the pump. Upon identifying such motion in the cavity section 120 by the motion sensor of the PCB 111, sanitizer may be dispensed onto a person's hand, or another item. In one embodiment, PCB 111 may be combined to eliminate the need for two PCBs. The cavity section 120 may also dispense sanitizer without a motion sensor utilizing a mechanical pump or lever to extract out the sanitizer, in one embodiment. Any type of dispensing method may be utilized for the sanitizer. In another embodiment, the cavity section may also house an ultraviolet light, which has known capabilities for disinfecting viruses, bacteria, germs, etc. The cavity section 120 may also include lighting capabilities to allow for visibility in darker settings. In one embodiment, which may include the apparatus 100 that is hanging or attached to a wall or other surface, the cavity section 120 may not include a bottom portion given that it does not to be supported by a bottom surface. Thus, the cavity section 120 does not necessarily include a bottom portion that provides support for stability on a top surface (e.g., table, counter, etc.).

The sanitizer may be stored in a sanitizer tank 115. The sanitizer tank 115 may abut with the main base 118. The sanitizer tank 115 may be utilized to store sanitizers or other liquids that may be utilized to eliminates germs, viruses, bacteria, etc. The sanitizer tank 115, for example, may store liquid soap in one embodiment. The sanitizer tank 115 may be encapsulate into the main base 118 in order to be stored properly. The sanitizer tank 115 may be covered by a tank lid that is removable to allow refilling of sanitizer or other liquids, and to protect impurities from entering the tank. The sanitizer tank 115 may be any size, for example, have capacity for 300 mL of liquid. The sanitizer tank 115 may have the sanitizer be extracted via a pump including a motor 119 that is utilized to pump the liquid from the tank 115 via a disperser tube 117. The disperser tube 117 may be in communication with both the tank 115 and the cavity section 120. The dispersed tube 117 may be connected to an outlet or opening 125 at the cavity section 120 to allow the liquid from the tank 115 to be dispersed from the tank 115 to the user. Thus, when the motor 114 is actuated by a user seeking to obtain a liquid sanitizer via a sensor 131 (e.g., motion sensor) or any other mechanism (e.g., a mechanical lever), the motor 114 may actuate and cause liquid to be pulled from the tank 115 through the disperser tube 117 and out of the outlet 125. The motor 114 may allow for 3 dispensing volume levels (e.g., low, medium, high) of the liquid that may be adjusted via the buttons 119.

The main base 118 may include an area for an energy storage device 121, which may include batteries or battery packs, solar cells, or other energy storage devices. Such options in the energy storage device 121 may allow for portability. In one embodiment, the batteries utilized may be rechargeable batteries that may be reused when power is depleted. The apparatus 101 may include a connection to allow charging of the energy storage device 121 via an AC adapter, USB cable, or any other interface. The energy storage device 121 may also utilize a power supply (e.g., AC adapter) that allows hard-wired connection into to a receptacle for operation.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An apparatus configured to purify air and sanitize, comprising:
    a main base;
    a lid including one or more ventilation perforations to intake air and an orifice to output purified air;
    a filter configured to remove at least bacteria from atmospheric air and extract purified air;
    a fan configured to intake atmospheric air into the filter and blow a purified air extracted from the filter and out of the lid;
    a tank located in the main base and configured to store liquid, wherein the liquid includes at least liquid sanitizer;
    a pump, wherein the pump is configured to output liquid stored in the tank located in the main base; and
    a cavity section, wherein the cavity section includes an outlet configured to output the liquid sanitizer utilizing the pump.

2. The apparatus of claim 1, wherein the lid is removable from the main base.

3. The apparatus of claim 1, wherein the fan is configured to blow the purified air at a same time the pump is outputting liquid to the outlet.

4. The apparatus of claim 1, wherein the pump includes a motor and a disperser tube.

5. The apparatus of claim 1, wherein the main base includes one or more interface buttons configured to adjust a fan speed, adjust a sanitizing dispensing amount, or power off the apparatus.

6. The apparatus of claim 1, wherein the apparatus includes one or more circuit boards connected to the fan and the pump.

7. The apparatus of claim 1, wherein the apparatus includes one or more energy storage devices to operate the apparatus, wherein the one or more energy storage devices includes at least a battery.

8. The apparatus of claim 1, wherein the apparatus includes a motion sensor, wherein the pump is configured to output liquid from the tank to the outlet in response to activation of the motion sensor.

9. An apparatus configured to purify air and sanitize, comprising:
    a fan configured to intake atmospheric air into a filter and blow purified air extracted from the filter and out of a lid, wherein the lid is encircled with a plurality of perforations;
    a tank located in a main base and configured to store liquid, wherein the liquid includes at least liquid sanitizer;
    a pump, wherein the pump is configured to output liquid stored in the tank located in the main base; and
    an outlet configured to output the liquid sanitizer in response to actuations of the pump.

10. The apparatus of claim 9, wherein the apparatus includes a main base including one or more buttons configured to operate the apparatus.

11. The apparatus of claim 10, wherein the main base includes a cavity section, wherein the cavity section includes the outlet.

12. The apparatus of claim 9, wherein the fan is arranged on top of the filter and closer to an orifice, and the fan is a substantially similar diameter to the filter.

13. The apparatus of claim 9, wherein the apparatus includes a battery pack configured to supply power to at least the pump and the fan.

14. The apparatus of claim 9, wherein the apparatus includes a filter adjacent to the one or more ventilation perforations and is enclosed in the lid.

15. The apparatus of claim 9, wherein apparatus includes a lid attachable to the main base, wherein the lid includes an opening to intake air at and one or more ventilation perforations to output purified air.

16. An apparatus configured to purify air and sanitize, comprising:
    a main base including one or more buttons configured to operate the apparatus;
    a lid, wherein the lid includes a bottom that is attachable to a top section of the main base, wherein the lid includes one or more ventilation perforations to intake air and an opening to output purified air;
    a filter enclosed in the lid, wherein the filter is configured to extract purified air;
    a fan configured to intake atmospheric air into the filter and blow purified air extracted from the filter;
    a tank configured to store liquid, wherein the liquid includes at least liquid sanitizer;
    a pump, wherein the pump is configured to output liquid stored in the tank.

17. The apparatus of claim 16, wherein the pump is located in the main base.

18. The apparatus of claim 16, wherein the pump includes a motor and a dispenser tube, wherein the dispenser tube includes a first end located in the sanitizer tank and a second end connected to the outlet.

19. The apparatus of claim 16, wherein the one or more ventilation perforations encircle the lid in a 360 degree manner.

20. The apparatus of claim 16, wherein the apparatus includes a cavity section that includes an outlet configured to output the liquid santizer.

* * * * *